(12) United States Patent
Blanpied et al.

(10) Patent No.: US 9,841,530 B2
(45) Date of Patent: Dec. 12, 2017

(54) MATERIAL DISCRIMINATION USING SCATTERING AND STOPPING OF MUONS AND ELECTRONS

(71) Applicant: Decision Sciences International Corporation, Poway, CA (US)

(72) Inventors: Gary Blanpied, Ramona, CA (US); Sankaran Kumar, San Marcos, CA (US); Dustin Dorroh, Ramona, CA (US); Craig Morgan, El Cajon, CA (US)

(73) Assignee: Decision Sciences International Corporation, Poway, CA (US)

( * ) Notice: Subject to any disclaimer, the term of this patent is extended or adjusted under 35 U.S.C. 154(b) by 305 days.

(21) Appl. No.: 14/822,825

(22) Filed: Aug. 10, 2015

(65) Prior Publication Data

US 2016/0041297 A1 Feb. 11, 2016

Related U.S. Application Data

(60) Provisional application No. 62/036,034, filed on Aug. 11, 2014.

(51) Int. Cl.
*G01V 5/00* (2006.01)
*G01N 23/20* (2006.01)
*G01N 23/08* (2006.01)

(52) U.S. Cl.
CPC ............ *G01V 5/005* (2013.01); *G01N 23/08* (2013.01); *G01N 23/20083* (2013.01);
(Continued)

(58) Field of Classification Search
USPC .................................................. 250/306, 307
See application file for complete search history.

(56) References Cited

U.S. PATENT DOCUMENTS 7,945,105 B1   5/2011   Jaenisch
8,247,767 B2   8/2012   Morris et al.
(Continued)

FOREIGN PATENT DOCUMENTS

WO   2014/051895 A2   4/2014
WO   2015/178986 A2   11/2015

OTHER PUBLICATIONS

Agostinelli, S., et al., "GEANT4—a simulation tool kit," Nuclear Instruments and Methods in Physics Research A, 506(3):250-303, Jul. 2003.
(Continued)

*Primary Examiner* — Kiet T Nguyen
(74) *Attorney, Agent, or Firm* — Perkins Coie LLP

(57) ABSTRACT

In one aspect, a process for characterizing a range of materials based on the scattering and stopping of incident cosmic ray charged particles passing through each material includes: determining a scattering metric and a stopping metric for each material within the range of materials exposed to cosmic ray charged particles; computing a ratio of the scattering metric to the stopping metric to obtain a scattering-to-stopping ratio for each material within the range of materials for the material; and establishing a scattering-stopping relationship for the range of materials based on the determined pairs of the scattering-to-stopping ratio and the associated scattering metric for the range of materials.

29 Claims, 6 Drawing Sheets

(52) U.S. Cl.
CPC .......... *G01V 5/0016* (2013.01); *G01V 5/0091* (2013.01); *G01N 2223/419* (2013.01)

(56) References Cited

U.S. PATENT DOCUMENTS

| | | | |
|---|---|---|---|
| 8,275,567 | B2 | 9/2012 | Lightfoot |
| 8,536,527 | B2 | 9/2013 | Morris et al. |
| 8,575,546 | B2 | 11/2013 | Nagamine |
| 2008/0191133 | A1 | 8/2008 | Morris et al. |
| 2008/0315091 | A1 | 12/2008 | Morris et al. |
| 2010/0310036 | A1 | 12/2010 | Burleton et al. |
| 2011/0127436 | A1 | 6/2011 | Hashizume et al. |
| 2011/0135180 | A1 | 6/2011 | Sugrue et al. |
| 2011/0216945 | A1 | 9/2011 | Jaenisch |
| 2011/0248163 | A1 | 10/2011 | Morris et al. |
| 2014/0319365 | A1 | 10/2014 | Sossong et al. |
| 2015/0241593 | A1 | 8/2015 | Blanpied et al. |
| 2015/0325013 | A1* | 11/2015 | Patnaik ................ G06T 7/11 345/424 |

OTHER PUBLICATIONS

Allison, J., et al., "Geant4 Developments and Applications," IEEE Transactions on Nuclear Science, 53(1):270-278, Feb. 2006.

Beringer, J., et al., "Cosmic Rays," Particle Data Group, Physical Review D, 86(1):1-21, Jun. 2012 [accessed at http://pdg.lbl.gov/2012/reviews/rpp2012-rev-cosmic-rays.pdf ].

Beringer, J., et al., "Passage of particles through matter" Particle Data Group, Physical Review D, 86(1):1-42, Jun. 2012 [accessed at http://pdg.lbl.gov/2013/reviews/rpp2012-rev-passage-particles-matter.pdf].

Borozdin, K. N., et al., "Surveillance: Radiographic Imaging with Cosmic Ray Muons," Nature, 422:277-278, Mar. 2003.

Grimani, C., et al., "Measurements of the absolute energy spectra of cosmic-ray positrons and electrons above 7 GeV," Astronomy and Astrophysics, 392(1):287-294, Sep. 2002.

International Search Report and Written Opinion dated Nov. 12, 2015 for International Application No. PCT/US2015/044531, filed on Aug. 10, 2015 (8 pages).

International Search Report and Written Opinion dated Nov. 27, 2015 for International Application No. PCT/US2015/017846, filed on Feb. 26, 2015 (7 pages).

Morris, C.L., et al., "Tomographic Imaging with Cosmic Ray Muons," Science & Global Security, 16(1-2):37-53, Oct. 2008.

Morris, C.L., et al., "Obtaining material identification with cosmic ray radiography," arXiv:1210.6102, 10 pages, Oct. 2012 [retrieved on Oct. 10, 2015] <URL: http://arxiv.org/abs/1210.6102>.

\* cited by examiner

MATERIAL DISCRIMINATION USING SCATTERING AND STOPPING OF MUONS AND ELECTRONS

CROSS REFERENCE TO RELATED APPLICATIONS

This patent document claims the benefit of priority of U.S. Provisional Patent Application No. 62/036,034, filed on Aug. 11, 2014. The entire contents of the before-mentioned patent application is incorporated by reference as part of the disclosure of this document.

TECHNICAL FIELD

The subject matter described in this disclosure generally relates to systems, devices, and processes for imaging and sensing based on cosmic-ray tomography. More specifically, the present disclosure provides a technique for applying cosmic-ray tomography in a manner that can detect and characterize not only dense assemblages of heavy nuclei but also lighter metals of commercial interest, such as silver, gold and platinum.

BACKGROUND

Cosmic ray imaging and sensing are techniques which exploit the multiple Coulomb scattering of highly penetrating cosmic ray-produced charged particles such as muons to perform non-destructive inspection of the material without the use of artificial radiation. The Earth is continuously bombarded by energetic stable charged particles, mostly protons, coming from deep space. These charged particles interact with atoms in the upper atmosphere to produce showers of charged particles that include many short-lived pions which decay producing longer-lived muons. Muons interact with matter primarily through the Coulomb force having no nuclear interaction and radiating much less readily than electrons. Such cosmic ray-produced charged particles slowly lose energy through electromagnetic interactions. Consequently, many of the cosmic ray produced muons arrive at the Earth's surface as highly penetrating charged radiation. The muon flux at sea level is about 1 muon per $cm^2$ per minute.

As a muon moves through material, Coulomb scattering off of the charges of sub-atomic particles perturb its trajectory. The total deflection depends on several material properties, but the dominant effects are the atomic number, Z, of nuclei and the density of the material. The trajectories of muons are more strongly affected by materials that make good gamma ray shielding, such as lead and tungsten, and by special nuclear materials (SNM), such as uranium and plutonium, than by materials that make up more ordinary objects such as water, plastic, aluminum and steel. Each muon carries information about the objects that it has penetrated. The scattering of multiple muons can be measured and processed to probe the properties of these objects. A material with a high atomic number Z and a high density can be detected and identified when the material is located, inside low-Z and medium-Z matter.

Coulomb scattering from atomic nuclei in matter results in a very large number of small angle deflections of charged particles as they transit the matter. In some examples, a correlated distribution function can be used to approximately characterize the displacement and angle change of the trajectory that depends on the density and the atomic charge of the material. As an example, this distribution function can be approximated as a Gaussian distribution. The width of the distribution function is proportional to the inverse of the momentum of the charged particle and the square root of the real density of material measured in radiation lengths. The correlated distribution function of cosmic ray-produced muons can provide information on materials in the paths of the muons with no radiation dose above the Earth's background and proper detection of such cosmic ray-produced muons can be implemented in a way that is especially sensitive to selected materials to be detected such as good radiation shielding materials.

In some examples of cosmic ray imaging and sensing, a muon tomography system can perform tomography of a target object under inspection based on scattering of muons by the target object. For example, muon tomography systems can be used for detecting certain targeted objects, e.g., such as materials that can be used to threaten the public, including smuggled nuclear materials. Muon tomography detector systems can be used jointly with or as an alternative to other nuclear material detectors such as gamma or X-ray detectors. Gamma and X-ray detectors operate by directing Gamma and X-ray radiation to a target object and measuring penetrated Gamma and X-ray radiation. Shielding of nuclear materials can reduce the count rates in the Gamma and X-ray detectors and reduce the detection performance of Gamma and X-ray detectors. Muon tomography detection systems can detect shielded nuclear materials and objects.

An exemplary charged particle tomography detection system can include cosmic ray charged particle detectors to detect and track ambient cosmic ray produced charged particles, such as muons, traversing through a volume of interest (VOI). The cosmic ray charged particle detectors can include an array of drift-tube sensors to enable tomographic imaging of the VOI. Cosmic ray charged particles, e.g., primarily muons and electrons, shower through the VOI, and measurement of individual particle tracks can be used to reconstruct the three-dimensional distribution of atomic number (Z) and density of materials in the VOI using particle scattering.

SUMMARY

Techniques, systems, and devices are disclosed for characterizing a range of materials based on the scattering and stopping of incident cosmic ray charged particles passing through each material, and for detecting and identifying contents of a VOI exposed to cosmic ray charged particles based on the characterized scattering and stopping relationship for the range of materials.

In one aspect, a process for characterizing a range of materials based on the scattering and stopping of incident cosmic ray charged particles passing through a material within a range of materials is disclosed. The process includes determining a scattering metric and a stopping metric for the material exposed to cosmic ray charged particles. The process includes creating a VOI of the material. The process includes determining a scattering metric of cosmic ray charged particles interacting with the VOI of the material to represent a first set of cosmic ray charged particles entering and exiting the VOI of the material. Also, the process includes determining a stopping metric of cosmic ray charged particles interacting with the VOI of the material to represent a second set of cosmic ray charged particles entering and stopping inside the VOI of the material. The process includes computing a ratio of the determined scattering metric to the stopping metric to obtain a scattering-to-stopping ratio for the material. In addition, the process includes establishing a scattering-stopping relationship of cosmic ray charged particles for the material based on the determined pairs of the scattering-to-stopping ratio and the associated scattering metric for the material.

In some implementations, the process includes establishing the scattering-stopping relationship by plotting the scattering-to-stopping ratio against the scattering metric.

In some implementations, the plotted relationship of the scattering-to-stopping ratio versus the scattering metric is substantially linear over the range of materials. A greater scattering-to-stopping ratio corresponds to a greater density of the associated material.

In some implementations, the process includes determining the scattering metric by: obtaining a set of scattering angles for the set first of cosmic ray charged particles; computing an average scattering angle of the set of scattering angles; determining an average momentum of the incident cosmic ray particles; and determining the scattering metric based on the average scattering angle and the average momentum.

In some implementations, the process includes normalizing the scattering metric by the thickness of the VOI of the material.

In some implementations, the process includes determining the stopping metric by: obtaining a raw stopping number of a set of cosmic ray charged particles entering and stopping inside the VOI; obtaining a scattering number of a set of cosmic ray charged particles entering and exiting the VOI; and determining the stopping metric by normalizing the raw stopping number by the scattering number to compensate for the undetected scattered cosmic ray particles.

In some implementations, the process includes normalizing the stopping metric by the thickness of the VOI of the material.

In some implementations, the process includes multiplying the stopping metric by an average momentum of the incident cosmic ray particles.

In some implementations, the cosmic ray charged particles include cosmic ray muons and/or cosmic ray electrons.

In some implementations, the cosmic ray produced muons are used to characterize metals in the range of materials having densities greater than the density of aluminum.

In some implementations, the characterized metals include special nuclear materials (SNM) such as uranium, and metals of commercial interests, such as silver, gold and platinum.

In some implementations, the cosmic ray produced electrons are used to characterize materials having densities substantially equal to or less than the density of aluminum.

In another aspect, a process for identifying a material of a VOI exposed to cosmic ray charged particles includes determining a scattering metric of cosmic ray charged particles interacting with the VOI to represent a first set of cosmic ray charged particles entering and exiting the VOI. The process includes determining a stopping metric of cosmic ray charged particles interacting with the VOI to represent a second set of cosmic ray charged particles entering and stopping inside the VOI. The process includes computing a ratio of the scattering metric to the stopping metric to obtain a scattering-to-stopping ratio for the VOI. In addition, the process includes comparing the determined pair of scattering-to-stopping ratio and the scattering metric against an established relationship between the scattering-to-stopping-ratio and the scattering metric for a range of known materials to determine whether the material of the VOI matches a material in the range of known materials.

In some implementations, the process includes determining the scattering metric by: obtaining a set of scattering angles for the first set of cosmic ray charged particles. The process includes computing an average scattering angle of the set of scattering angles. The process includes determining an average momentum of the incident cosmic ray charged particles; and determining the scattering metric based on the average scattering angle and the average momentum.

In some implementations, the process includes normalizing the scattering metric by a thickness of the VOI of the material.

In some implementations, the process includes determining the stopping metric by: obtaining a raw stopping number of a set of cosmic ray charged particles entering and stopping inside the VOI; obtaining a scattering number of a set of cosmic ray charged particles entering and exiting the VOI; and determining the stopping metric by normalizing the raw stopping number by the scattering number to compensate for the undetected scattered cosmic ray particles.

In some implementations, the process includes normalizing the stopping metric by the thickness of the VOI of the material.

In some implementations, the process includes multiplying the stopping metric by an average momentum of the incident cosmic ray charged particles.

In some implementations, the cosmic ray charged particles include cosmic ray produced muons and/or cosmic ray produced electrons.

In some implementations, the cosmic ray produced muons are used to detect the VOI for target metals having densities greater than the density of aluminum.

In some implementations, the target metals include special nuclear materials (SNM) such as uranium and metals of commercial interest, such as silver, gold and platinum.

In some implementations, cosmic ray produced electrons are used detect the VOI for target metals having densities substantially equal to or less than the density of aluminum.

In some implementations, the process includes, after identifying the material of the VOI, inferring the thickness of the VOI based on an established relationship between the scattering-to-stopping-ratio and a normalized stopping metric per unit thickness for the range of known materials.

Figure 1:
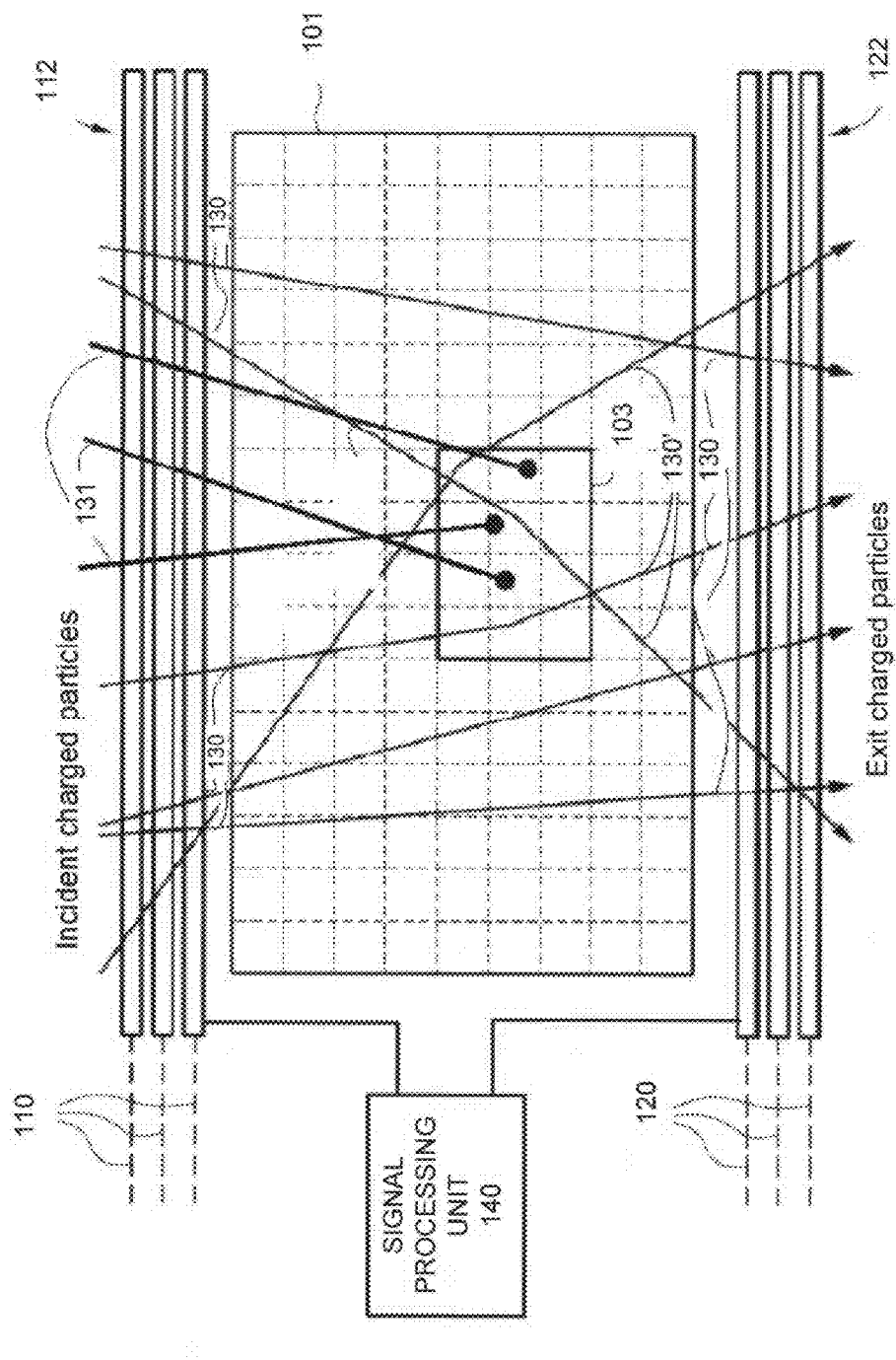
FIG. 1 shows an exemplary cosmic-ray particle tomography system in accordance with some embodiments described herein.

exposed to cosmic ray particles in accordance with some embodiments described herein.

DETAILED DESCRIPTION

Disclosed are techniques, systems, and devices for characterizing a range of materials based on the scattering and stopping of incident cosmic ray particles passing through the range of materials, and for detecting and identifying contents of a volume of interest (VOI) exposed to cosmic ray charged particles based on the characterized scattering and stopping relationship for the range of materials.

In one aspect, a process for characterizing a range of materials based on the scattering and stopping of incident cosmic ray particles passing through a given material is disclosed. The process includes determining a scattering metric and a stopping metric for the material within the range of materials exposed to cosmic ray charged particles. The process includes creating a VOI of the material exposed to cosmic ray charged particles. The process includes determining a scattering metric of cosmic ray charged particles interacting with the VOI of the material exposed to cosmic ray charged particles to represent a first set of cosmic ray charged particles entering and exiting the VOI of the material exposed to cosmic ray charged particles. The process includes determining a stopping metric of cosmic ray charged particles interacting with the VOI of the material exposed to cosmic ray charged particles to represent a second set of cosmic ray charged particles entering and stopping inside the VOI of the material exposed to cosmic ray charged particles. The process includes computing a ratio of the scattering metric to the stopping metric to obtain a scattering-to-stopping ratio for the material exposed to cosmic ray charged particles. The process includes establishing a scattering-stopping relationship of cosmic ray charged particles for the range of materials based on the determined pairs of the scattering-to-stopping ratio and the associated scattering metric for the range of materials exposed to cosmic ray charged particles.

In another aspect, a process for identifying a material of a VOI exposed to cosmic ray charged particles includes determining a scattering metric of cosmic ray particles interacting with the VOI to represent a first set of cosmic ray particles entering and exiting the VOI. The process includes determining a stopping metric of cosmic ray charged particles interacting with the VOI to represent a second set of cosmic ray charged particles entering and stopping inside the VOI. The process includes computing a ratio of the scattering metric to the stopping metric to obtain a scattering-to-stopping ratio for the VOI. The process includes comparing the determined pair of scattering-to-stopping ratio and the scattering metric against an established scattering-to-stopping-ratio versus the scattering metric relationship for a range of materials to determine whether the material of the VOI matches a material in the range of materials.

Cosmic ray produced charged particles (such as electrons and muons) passing through a VOI associated with a matter interact by scattering from the atoms of the matter and by being absorbed by them ("stopping"). Comparison of the stopping and scattering signals in the VOI can potentially be used as a diagnostic tool for identifying metals, or for classifying materials as low, medium or high density. A technique relying primarily on the muon component of cosmic rays can be used to interrogate a Volumes of Interest (VOI). Because muons are highly energetic and massive, muons can pass essentially un-scattered through materials of light atomic mass and are typically only weakly scattered by conventional metals used in industry (e.g., aluminum, iron, steel, and the like). Substantial scattering and absorption generally only occur when muons encounter sufficient thicknesses of heavy elements such as lead and special nuclear materials (SNM), as well as silver, gold and platinum.

Also, techniques can be implemented to construct relationship between scattering and stopping of cosmic-ray charged particles over a wide range of atomic masses and material densities. Due to the differing behaviors of cosmic ray produced muons and electrons when scattering and stopping in different atomic mass materials, a cosmic ray tomography system can be implemented to use cosmic ray produced muons and electrons to respectively detect medium to high and low atomic-mass materials. For example, cosmic-ray muon detection techniques may be used to obtain scattering and stopping signals for medium atomic mass materials and high-atomic-mass material. Such medium and high atomic-mass materials can include heavier metals, such as SNM and light metals, such as gold, platinum and silver, as well as industrial metal parts. The variation of muon scattering as a function of atomic mass and density can be used for differentiating heavier metals, such as SNM and light metals, such as gold, platinum and silver, as well as industrial metal parts. In addition, cosmic-ray electron detection techniques may be used to obtain scattering and stopping signals for low atomic mass materials, such as organic materials, drugs and explosives.

In this disclosure, terms "a low atomic mass material," "a low-atomic-mass material" and "a low density material" can refer to both a material made of a single low-atomic-mass element such as carbon and oxygen, and a compound or a mixture having a low density, such as organic materials, drugs and explosives. Similarly, terms "a medium atomic mass material," "a medium-atomic-mass material" and "a medium density material" can refer to either a material made of a single medium-atomic-mass element such as aluminum and iron, or a compound or a mixture having a medium density, such as steel and some other alloys. In addition, terms "a high atomic mass material," "a high-atomic-mass material" and "a high density material" can refer to either a material made of a single high-atomic-mass element such as lead, tungsten, uranium and plutonium, or a compound or a mixture having a high density, such as high density alloys. In some implementations, low density or low atomic mass material refers to any material with density substantially equal to or less than that of aluminum. Therefore, these low density materials can include all organic materials, including but not limited to contraband such as illegal drugs and conventional explosives.

The cosmic-ray charged particle detection systems, devices and methods described in this application can be implemented to detect presence of certain objects or materials such as nuclear materials and to obtain tomographic information of such objects or materials in various applications including but not limited to inspecting packages, containers, occupied vehicles at security check points, border crossings and other locations for nuclear threat objects that may range from fully assembled nuclear weapons to small quantities of highly shielded nuclear materials. Features described in this application can be used to construct various particle detection systems.

For example, a particle detection system can include an object holding area for placing an object to be inspected, a first set of position sensitive cosmic-ray charged particle detectors at a first location with respect to the object holding area to measure positions and directions of incident or incoming cosmic-ray charged particles entering the object holding area, a second set of position sensitive cosmic-ray charged particle detectors at a second location with respect to the object holding area opposite to the first location to measure positions and directions of outgoing cosmic-ray charged particles exiting the object holding area, and a signal processing unit, which may include, e.g., a microprocessor, to receive data of measured signals associated with the incoming muons from the first set of position sensitive cosmic-ray charged particle detectors and measured signals associated with the outgoing cosmic-ray charged particles from the second set of position sensitive particle detectors. As an example, the first and second sets of position sensitive cosmic ray charged particle detectors can be implemented to include drift tubes arranged to allow at least three charged particle positional measurements in a first direction and at least three charged particle positional measurements in a second direction different from the first direction. The signal processing unit can analyze scattering behaviors of the cosmic-ray charged particles caused by scattering of the cosmic-ray charged particles in the objects or materials within the object holding area based on the measured incoming and outgoing positions and directions of the incoming and outgoing cosmic-ray charged particle to obtain a tomographic profile or the spatial distribution of scattering centers within the object holding area.

The obtained tomographic profile or the spatial distribution of scattering centers can be used to reveal the presence or absence of one or more objects or materials in the object holding area such as materials with high atomic numbers including nuclear materials or devices. The first and second position sensitive cosmic ray charged particle detector can be implemented in various configurations, including drift cells such as drift tubes filled with a gas which can be ionized by muons. Such a system can be used to utilize naturally occurring cosmic-ray charged particles as the charged particle source for detecting one or more objects or materials in the object holding area.

In applications for portal monitoring, the illustrative embodiments provide an approach to potentially enable robust nuclear material detection at reduced cost and with increased effectiveness. Furthermore, the approach can potentially provide a radiation portal monitor which is capable of determining whether a given vehicle or cargo is free of nuclear threats by both measuring the absence of a potential shielded package and the absence of a radiation signature.

The portal monitoring systems shown in the accompanying drawings employ cosmic ray-produced charged particle tracking with drift tubes. As will be explained in more detail below, the portal monitoring systems utilize drift tubes to enable tracking of cosmic ray charged particles, such as muons and electrons, passing through a volume as well as detection of gamma rays. Advantageously, these portal monitoring systems can effectively provide the combined function of a cosmic ray radiography apparatus with passive or active gamma radiation counter to provide a robust detector for nuclear threats. This eliminates the need for two separate instruments.

Cosmic ray-produced muons and electrons can provide information with no radiation dose above the earth's background and proper detection of such cosmic ray-produced charged particles such as muons and electrons can be implemented in a way that is especially sensitive to good shielding materials. A detection system can be configured to perform tomography of a target object under inspection based on scattering of muons and electrons by the target object. The system can be configured to perform tomography to localize scattering. The tomographic position resolution can be expressed approximately as follows:

$$\Delta x = \theta_{RMS} L$$

where:

$\theta_{RMS}$=the root-mean-square (rms) of the scattering angle, and

L=the size of the volume under the detection by the detection apparatus.

For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta \theta}{\theta} = \frac{1}{\sqrt{2N}}$$

where:

$\theta$=the rms scattering angle,

N=number of cosmic ray-produced muons and/or electrons passing through a region of interest.

For example, the angular resolution for N=100 (corresponding to a 10×10 cm² resolution element after one minute of counting) is $\Delta \theta$=0.07$\theta$.

Tomographic methods, designed to construct an image or model of an object from multiple projections taken from different directions, can be implemented in the cosmic ray charged particle detection system to provide a discrete tomographic reconstruction of the volume of interest based on the data provided by the cosmic-ray charged particles entering and exiting the volume of interest. In some implementations, Monte Carlo simulation techniques can be used to study applications and shorten scanning times. Other stochastic processing methods may also be used in implementing the cosmic ray tomographic imaging described in this application.

The cosmic ray charged particle radiography function of the particle detection systems of the embodiments can be more readily understood with reference to examples of detection systems adapted to detect cosmic ray-produced charged particles such as those shown in FIG. 1. FIG. 1 illustrates a detection system 100 for utilizing cosmic-ray charged particles to detect an object. System 100 includes a set of two or more planes or layers 110 of position sensitive incoming cosmic ray charged particle detectors 112 arranged above a volume 101 to be imaged for providing the position and angles (i.e., directions in the 3-D space) of incoming cosmic ray charged particle tracks 130 and 131. The incoming position sensitive charged particle detectors 112 can measure the position and angles of incoming cosmic ray charged particle tracks 130 and 131 with respect to two different directions, e.g., in two orthogonal coordinates along x and y axes. Cosmic ray charged particles (e.g., muons and electrons) pass through the volume 101 where the VOI 103 may be located and are scattered to an extent dependent upon the material occupying the volume 103 through which they pass. Another set of two or more planes or layers 120 of outgoing cosmic ray charged particle detectors 122 are positioned below the volume 101 and opposite to the planes or layers 110 of incoming cosmic ray charged particle detectors 112 to record outgoing or exiting cosmic ray charged particle positions and directions. The drift tubes in detectors 112 and 122 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks passing through the volume 101 in horizontal direction. The scattering angle of each charged particle is computed from the incoming and outgoing detector signal measurements.

A signal processing unit 140, e.g., a computer, is provided in the system 100 to receive data of measured signals of the incoming cosmic ray charged particles by the position sensitive cosmic ray charged particle detectors 112 and outgoing cosmic ray charged particles by the position sensitive cosmic ray charged particle detectors 122. The signal processing unit 140 can analyze the scattering of the cosmic ray charged particles in the volume 101 based on the measured incoming and outgoing positions and directions of cosmic ray charged particles to obtain a tomographic profile or the spatial distribution of the scattering density reflecting the scattering strength or radiation length within the volume 101. The obtained tomographic profile or the spatial distribution of the scattering density within the volume 101 can reveal the contents of the VOI 103 in the volume 101. FIG. 1 shows drift tube detectors 112 and 122 are located on top (above the volume 101) and bottom (below the volume 101) of the volume 101. In some implementations, additional drift tube detectors can be implemented on sides positioned laterally or horizontally with respect to the volume 101 to form a box or four sided detection structure into which a package, a vehicle or cargo container can enter for scanning by the system.

The signal processing unit 140 of system 100 in FIG. 1 and other systems described in this application can process signals received from the position sensitive cosmic ray charged particle detectors associated with cosmic ray charged particles traversing through a volume under inspection (e.g., a package, a container or a vehicle) to perform various operations. For example the signal processing unit 140 can process the signals received from the position sensitive cosmic ray charged particle detectors to reconstruct the trajectory of a cosmic ray charged particle such as a muon or an electron traversing through the volume 101. The signal processing unit 140 can process the signals received from position sensitive cosmic ray charged particle detectors 112 to measure the momentum of an incoming charged particle. The signal processing unit 140 can process the signals received from position sensitive cosmic ray charged particle detectors 122 to measure the momentum of an outgoing cosmic ray charged particle. The signal processing unit 140 can determine the spatial distribution of the scattering density of the volume 101. Results from the signal processing unit 140 processing the signals received from the position sensitive cosmic ray charged particle detectors 112 and 122 can be used to construct the tomographic profile and measure various properties of the volume 101.

For example, the process for reconstructing the trajectory of a cosmic ray charged particle traversing or passing through a cosmic ray charged particle detector having a set of drift cells can include obtaining hit signals representing identifiers of drift cells hit by charged particles and corresponding hit times. The cosmic ray charged particle trajectory reconstruction process can include grouping in-time drift cell hits identified as being associated with a track of a particular cosmic ray charged particle passing through the corresponding cosmic ray charged particle detector. The cosmic ray charged particle trajectory reconstruction process can include initially estimating a time zero value for a moment of time at which the particular cosmic ray charged particle hits a given drift cell. The cosmic ray charged particle trajectory reconstruction process can include determining drift radii based on estimates of the time zero values, drift time conversion data and the time of the hit. The cosmic ray charged particle trajectory reconstruction process can include fitting linear tracks to drift radii corresponding to a particular time zero value. Also, the cosmic ray charged particle trajectory reconstruction process can include searching and selecting a time-zero value associated with a perceived near best or ideal of the track fits performed for a particular charged particle and computing error in time-zero and tracking parameter. Reconstruction of the track based on the time zero fit provides a reconstructed linear trajectory of the cosmic ray charged particle passing through the position sensitive cosmic ray charged particle detector without having to use fast detectors (such as photomultiplier tubes with scintillator paddles) or some other fast detector which detects the passage of the muon through the apparatus to the nearest few nanoseconds to provide the time-zero.

Also, the processing for measuring the momentum of an incoming or outgoing cosmic ray charged particle based on signals from the position sensitive cosmic ray charged particle detectors (i.e., detector signals) can include, for example, configuring position sensitive cosmic ray charged particle detectors to scatter a cosmic ray charged particle passing through the position sensitive cosmic ray charged particle detectors. The process for measuring the momentum of an incoming or outgoing cosmic ray charged particle based on detector signals include measuring the scattering of a cosmic ray charged particle at the position sensitive cosmic ray charged particle detectors. Measuring the scattering can include obtaining at least three positional measurements of the scattering cosmic ray charged particle. The process for measuring the momentum of an incoming or outgoing cosmic ray charged particle based on detector signals include determining at least one trajectory of the cosmic ray charged particle from the positional measurements. In addition, the process for measuring the momentum of an incoming or outgoing cosmic ray charged particle based on detector signals include determining at least one momentum measurement of the cosmic ray charged particle from the at least one trajectory. This technique can be used to determine the momentum of the cosmic ray charged particle based on the trajectory of the cosmic ray charged particle. The trajectory of the cosmic ray charged particle is determined from the scattering of the cosmic ray charged particle at the position sensitive cosmic ray charged particle detectors themselves without the use of additional metal plates in the detector.

Also, the spatial distribution of the scattering density of the volume can be determined from cosmic ray charged particle tomographic data by obtaining predetermined cosmic ray charged particle tomography data corresponding to scattering angles and estimated momentum of cosmic ray charged particles passing through object volume. Determining the spatial distribution of the scattering density of the volume from cosmic ray charged particle tomographic data can include providing the probability distribution of cosmic ray charged particle scattering for use in an image reconstruction technique such as an expectation maximization (ML/EM) technique, the probability distribution being based on a statistical multiple scattering model. Also, determining the spatial distribution of the scattering density of the volume from cosmic ray charged particle tomographic data can include determining an estimate of the object volume density, e.g., by determining a substantially maximum likelihood estimate using the expectation maximization (ML/EM) technique. In addition, determining the spatial distribution of the scattering density of the volume from cosmic ray charged particle tomographic data can include outputting reconstructed object volume scattering density. The reconstructed object volume scattering density can be used to identify the presence and/or type of object occupying the volume of interest from the reconstructed volume density profile. Various applications include cosmic ray charged particle tomography for various homeland security inspection applications in which vehicles or cargo can be scanned by a charged particle tracker.

The tomographic processing part of the signal processing unit 140 may be implemented in a computer at the same location as the detectors 112 and 122. Alternatively, the tomographic processing part of the signal processing unit 140 may be implemented in a remote computer that is connected on a computer network such as a private network or a public network such as the Internet.

In FIG. 1, incoming cosmic ray charged particle detectors 112 can detect the X-Y position, angle, speed, and momentum of each of the incident cosmic ray charged particles 130 and 131 entering the volume 101, while outgoing cosmic ray charged particle detectors 122 can detect the X-Y position, angle, speed, and momentum of each of the exiting charged particles 130 passing through volume 101. The signal processing unit 140 can process the position, angle, speed, and momentum data collected by position sensitive cosmic ray charged particle detectors 112 and 122 to match each incident cosmic ray charged particle 130 with a corresponding exiting cosmic ray charged particle 130. Also, the signal processing unit 140 can process the position, angle, speed, and momentum data collected by position sensitive cosmic ray charged particle detectors 112 and 122 to identify those exiting cosmic ray charged particles 130 that are scattered by VOI 103, such as cosmic ray charged particles 130', and generate a scattering number for the incident cosmic ray charged particles. The signal processing unit 140 can process the position, angle, speed, and momentum data collected by position sensitive cosmic ray charged particle detectors 112 and 122 to identify incident cosmic ray charged particles 131 stopped inside VOI 103 and generate a stopping number for the incident cosmic ray charged particles.

Further detail of cosmic-ray particle tomography systems which can be used to detect and identify content of a VOI exposed to cosmic ray particles based on the measured scattering and stopping characteristics of the cosmic ray particles is described in U.S. Pat. No. 8,247,767 entitled "PARTICLE DETECTION AND APPLICATIONS IN SECURITY AND PORTAL MONITORING" filed on Oct. 26, 2007, the content of which is incorporated by reference as part of the specification of this application.

Figure 2A:
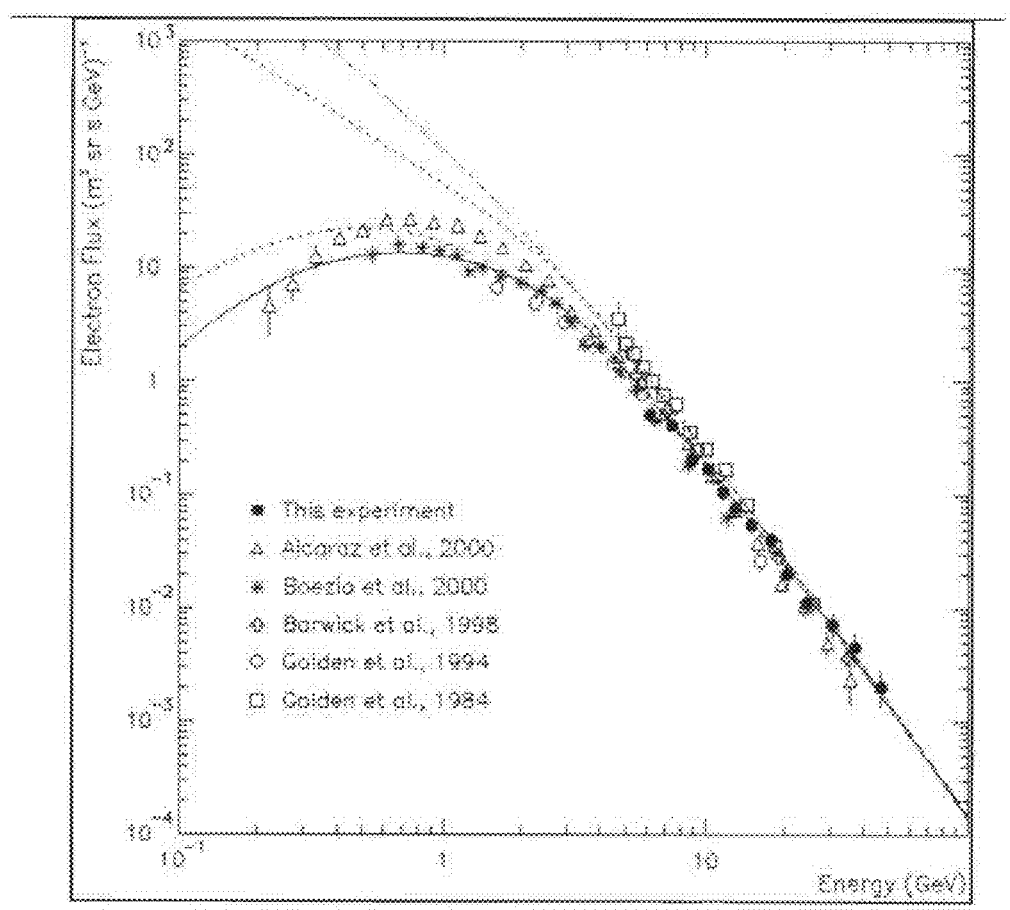
FIG. 2A shows a data plot of cosmic ray electron energy spectrum at sea level.
Figure 2B:
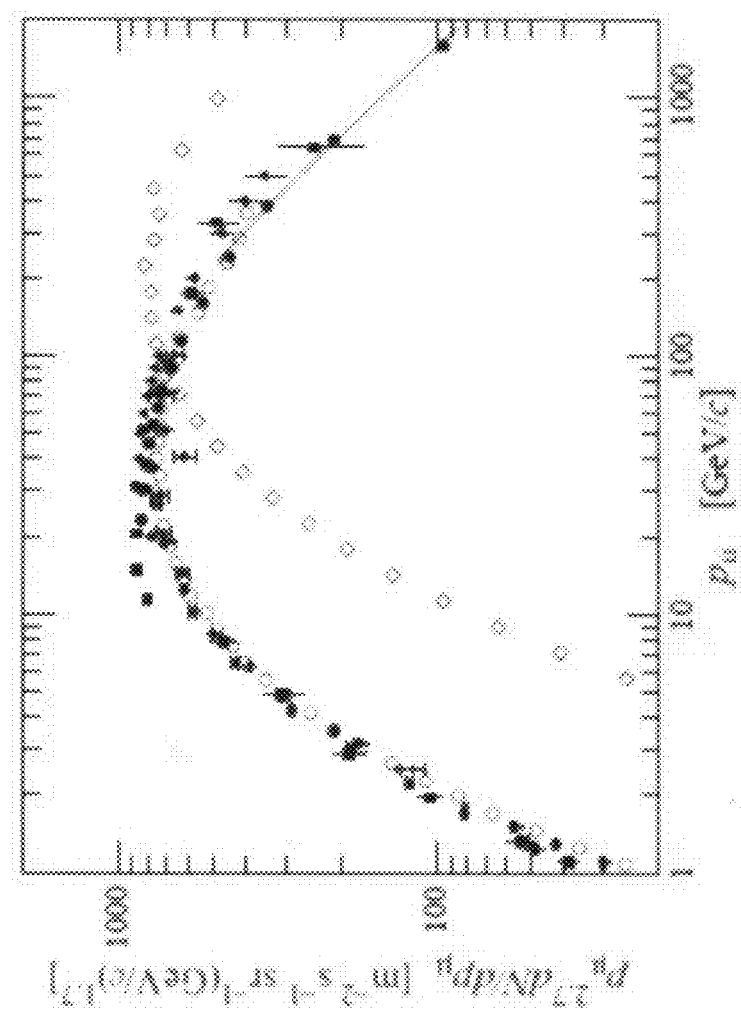
FIG. 2B shows a data plot of cosmic-ray muon momentum spectra for vertical (0°) and low-incident-angle (75°) muons.

The majority of cosmic-ray charged particles reaching the Earth's surface are electrons and muons produced as showers of secondary products of the interaction between more massive particles and the upper atmosphere. These two species of cosmic ray produced charged particles occupy substantially different parts of the energy spectrum, while some overlap can exist. FIG. 2A shows a data plot of cosmic ray electron energy spectrum at sea level (from C. Grimani et al., "Measurements of the absolute energy spectra of cosmic-ray positrons and electrons above 7 GeV", *Astron. Astrophys.* 392, 287-294, 2002). As shown in FIG. 2A, most electrons have energies between about 0.3 and 1 GeV (i.e., giga electron volts). FIG. 2B shows a data plot of cosmic-ray muon momentum spectra for vertical (0°) and low-incident-angle (75°) muons (from J. Beringer, "Cosmic Rays", Particle Data Group, Lawrence Berkeley Lab, 2012, accessed at pdg.lbl.gov/2012/reviews/rpp2012-rev-cosmic-rays.pdf). As can be seen in FIG. 2B, most muons have energies between about 0.5 and 200 GeV. Also, the plots show that electrons have a mean energy of about 0.7 GeV, and muons have a mean energy of about 3.7 GeV. The overlap in the electron and muon spectra represents a small fraction of the total flux.

One aspect of the present disclosure provides a technique for characterizing materials based on a ratio of a stopping power for an object to a scattering metric of the object. The stopping power may be defined by a technique disclosed in a co-pending provisional application, U.S. Provisional Patent Application No. 61/945,061, entitled, "Discrimination of Low-Atomic Weight Materials Using Scattering and Stopping of Cosmic-Ray Electrons," by inventor G. Blanpied et al., and filed on Feb. 26, 2014, the content of which is hereby incorporated by reference. Hence, the stopping power can be computed using the expression:

$$\text{Stopping Power} = \frac{(\text{raw number of stopped tracks/area/time}) \times \langle p \rangle}{(\text{number of scattered tracks/area/time}) \times \text{sample thickness}}, \quad (1)$$

where <p> is the average momentum of the incident cosmic rays.

In some implementations, the scattering metric is computed using the following expression:

$$\lambda = (\langle \theta \rangle \langle p \rangle)^2 / [\text{sample thickness}], \quad (2)$$

where <θ> is the average sample scattering angle. Note that this expression of the scattering metric allows for the elimination of sample thickness as an unknown. This is because the stopping power expression (1) is also normalized by the sample thickness, so that the ratio of the two eliminates the thickness variable. The above-described stopping power computation and scattering metric computation are used to obtain the data shown in FIGS. 3 and 4 below. In some embodiments, the ratio of stopping power to scattering enables material identification, and the mean scattering angle can be used to infer the sample thickness.

Figure 3:
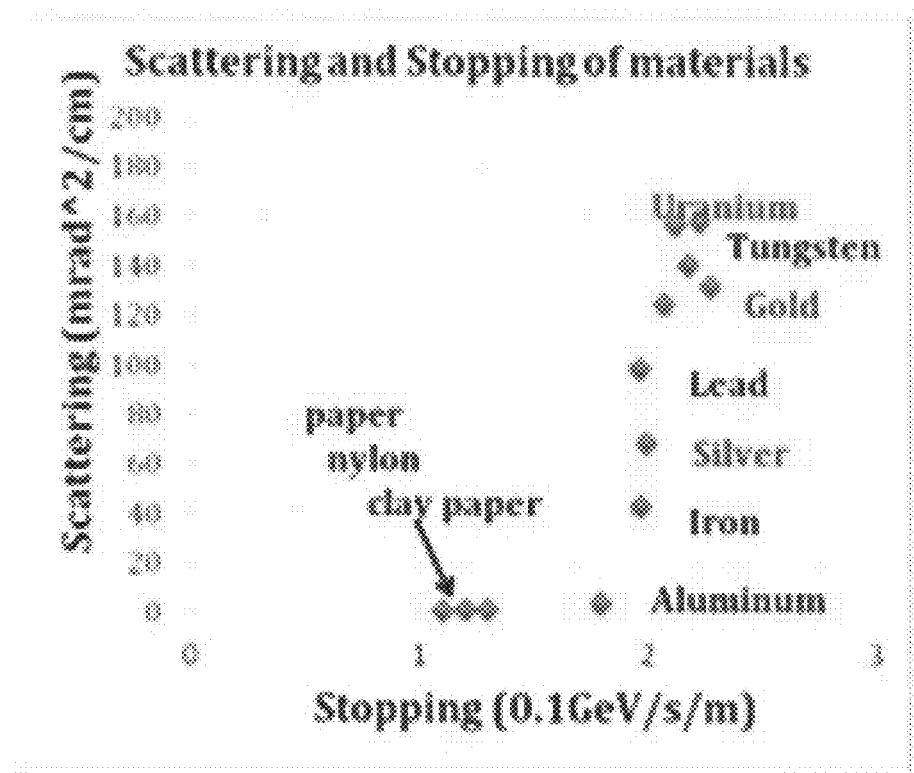
FIG. 3 shows the simulated data plot of scattering vs. stopping power of cosmic-ray particles for a wide range of materials using the GEANT program and DSIC's HMT drift-tube detector geometry in accordance with some embodiments described herein.

FIG. 3 shows the simulated data plot of scattering vs. stopping power of cosmic-ray particles for a wide range of materials using the GEANT program and DSIC's HMT drift-tube detector geometry in accordance with some embodiments described herein. Note that the scattering number represents cosmic ray produced charged particles (e.g., muons or electrons) that enter and subsequently exit the VOI which is calculated based on the average sample scattering angle; the stopping power represents cosmic ray produced charged particles that enters the VOI but are stopped inside the VOI. Simulated objects of medium and high density are 1 by 1 meter plates of 5.08 cm (2 inch) thickness. The simulated light objects are represented by 1 by 1 by 1 meter cubes. Objects are chosen to reduce geometry dependent (i.e., edge) effects. Note that the data shown in FIG. 3 display two regimes: (1) the low-density regime, comprising organic materials up to aluminum, is characterized by very little scattering but a strong variation in stopping power; and (2) the medium-to-high density regime which shows a larger variation in scattering power than in stopping power. Due to the differing behaviors of cosmic ray produced muon and electrons when scattering and stopping in different atomic mass materials, a cosmic ray tomography system can be implemented to use cosmic ray produced muons and electrons to respectively detect medium to high and low atomic-mass materials. For example, the cosmic ray produced muons can be used to characterize materials in the medium-to-high density regime having a density great than the density of aluminum, whereas the cosmic ray produced electrons can be used to characterize materials in the low density regime having a density substantially equal to or less than the density of aluminum. In this manner, atomic-mass based detection of materials using cosmic ray produced muons and electrons can provide a cosmic ray tomography system tailored to the scattering and stopping characteristics of cosmic ray produced muons and electrons.

Figure 4:
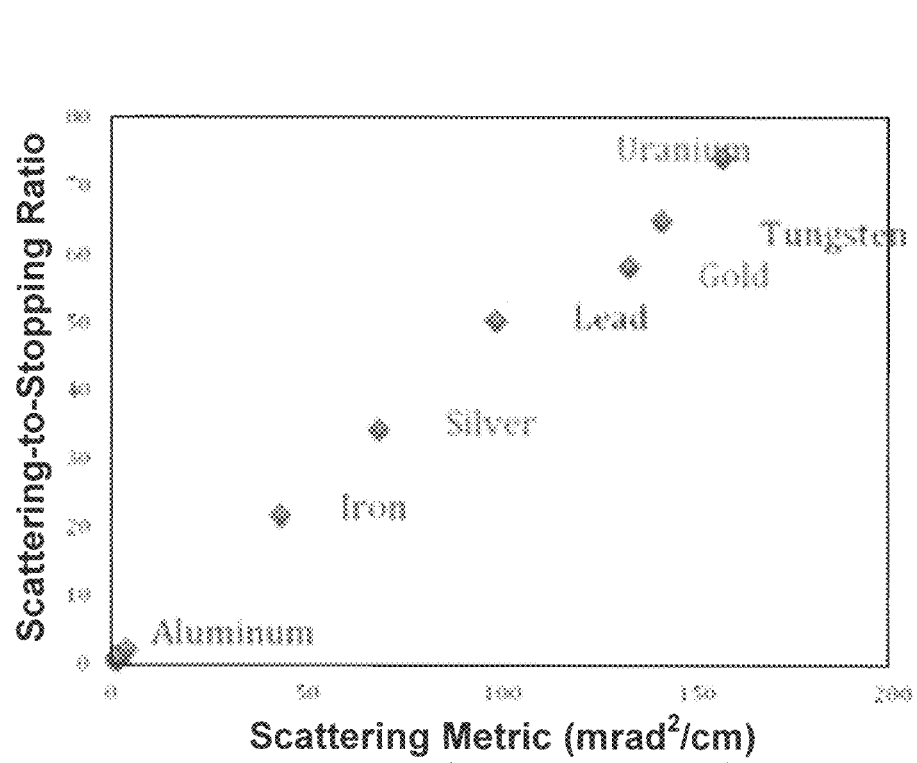
FIG. 4 shows a data plot of a ratio of the scattering power to the stopping power against the scattering power for cosmic-ray particles in accordance with some embodiments described herein.

FIG. 4 is a data plot showing an exemplary ratio of the scattering power to the stopping power against the scattering power for cosmic-ray produced charged particles in accordance with some embodiments described herein. The data plot demonstrates a clear monotonic (increasing with the atom-mass of the materials) and approximately linear relationship across a wide range of density and atomic mass. Ignoring geometric effects, the data plot of FIG. 4 suggests that the scattering/stopping ratio can be used as a reliable parameter to estimate the effective density or atomic mass of any given region in a tomography image, across a wide range of atomic masses.

The proposed technique can also be used to estimate the thickness of a detected material or object. The thickness of the detected material or object can be estimated by plotting the scattering/stopping ratio against stopping power per unit depth using the data from FIG. 3 and FIG. 4. The effective material thickness can be estimated from the absolute stopping value from the plot. Table 1 shows the estimated thickness of different metals in the form of plates of 5.08 cm thick in accordance with some embodiments described herein. Thickness values in the table are obtained by comparing the measured stopping to the average stopping of the 8 heaviest metals in the table. Inaccuracy of the estimates is generally less than 10% except for the lightest metal, aluminum. This degree of accuracy is useful in identifying the contents of the VOI. The errors in the technique may be reduced by more detailed analysis of the scattering/stopping ratios and correction for geometric effects.

TABLE 1

Estimated thickness of metal sheets, obtained from stopping power measurements.

| Metal | Estimated thickness (cm) | % error |
|---|---|---|
| Uranium | 5.06 | 1.2 |
| Tungsten | 5.19 | 3.8 |
| Gold | 5.42 | 8.5 |
| Platinum | 5.31 | 6.2 |
| Tantalum | 4.94 | -1.2 |
| Lead | 4.68 | -6.3 |
| Silver | 4.76 | -4.8 |
| Iron | 4.70 | -6.0 |
| Aluminum | 4.28 | -14.4 |

Figure 5:
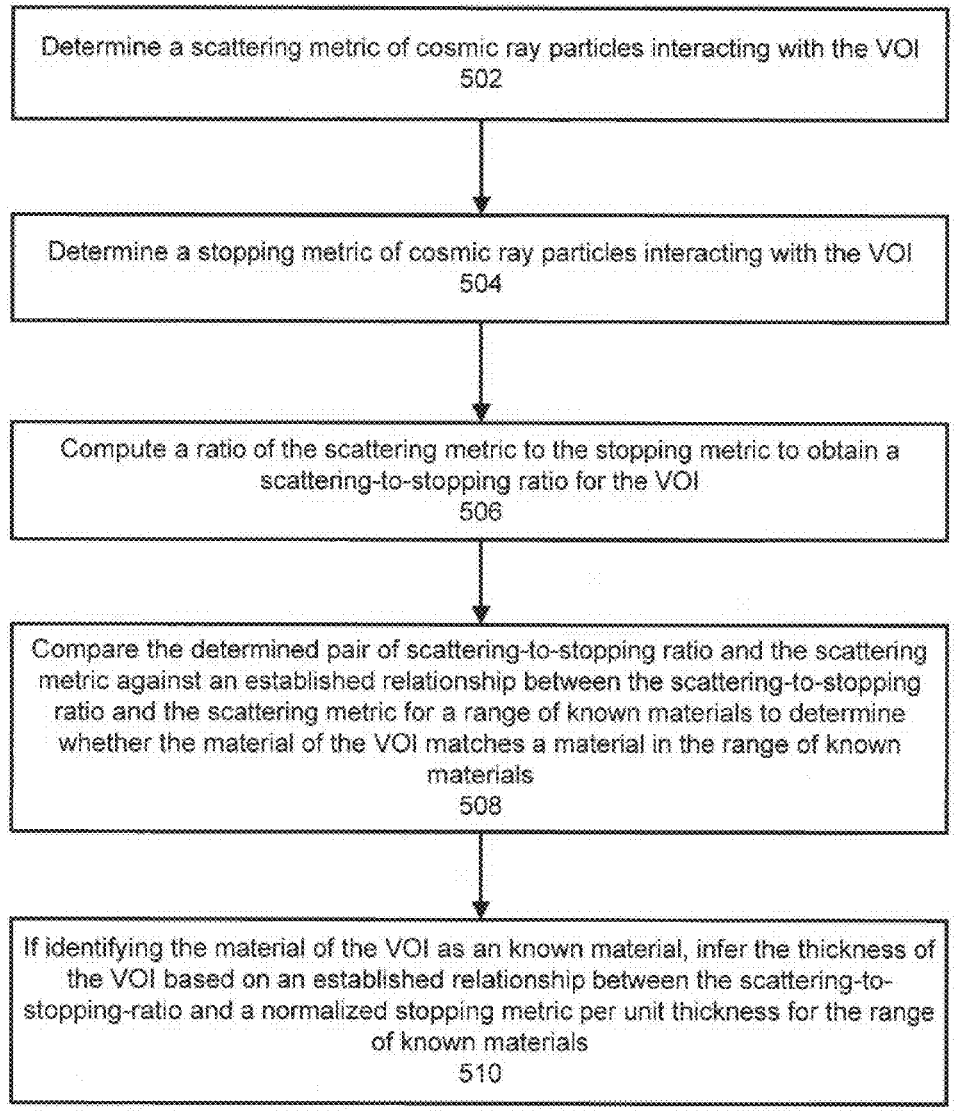
FIG. 5 presents a flowchart illustrating a process of identifying the material of a volume of interest (VOI)

FIG. 5 presents a flowchart illustrating an exemplary process of identifying a material or object of a VOI exposed to cosmic ray particles in accordance with some embodiments described herein. The material identifying process includes determining a scattering metric of cosmic ray charged particles interacting with the VOI to represent a first set of cosmic ray charged particles entering and exiting the VOI (502). For example, the scattering metric determining process can include using expression (2) to obtain the scattering metric. The material identifying process can include determining a stopping metric of cosmic ray particles interacting with the VOI to represent a second set of cosmic ray charged particles entering and stopping inside the VOI (504). For example, the stopping metric process can include using expression (1) to obtain the scattering metric. The material identifying process can include computing a ratio of the determined scattering metric to the determined stopping metric to obtain a scattering-to-stopping ratio for the VOI (506). The material identifying process includes comparing the determined pair of scattering-to-stopping ratio and the scattering metric against an established relationship between the scattering-to-stopping ratio and the scattering metric for a range of known materials or objects to determine whether the material of the VOI matches a material in the range of known materials (508). When identifying the material of the VOI as an known material, the process can include estimating a thickness of the material or object of VOI based on an established relationship between the scattering-to-stopping-ratio and a normalized stopping metric per unit thickness for the range of known materials (510).

The material identifying process can include a compensating or mitigating process for the geometric effects of the object being detected to improve the accuracy of the detection. For objects shaped like horizontal planes (e.g., sheets, slabs), substantially all of the cosmic ray produced charged particles traverse the same thickness (or are stopped by the same thickness) as they penetrate the objects. However, objects whose horizontal extent is comparable to or smaller than their vertical thickness can have a substantial number of cosmic ray charged particles with trajectories cutting through corners, and the path lengths of such cosmic ray charged particles can be much shorter than the path lengths of cosmic ray charged particles penetrating the entire thickness of the objects. This effect can skew the observed scattering and stopping power. This skewing, however, can be mitigated by repeating the data reduction, selecting different-sized subsets (i.e., masks) of the VOI for analysis. A mask much smaller than the full horizontal extend of an object will include a smaller fraction of cosmic ray charged particle trajectories cutting the corners, and thus have smaller systematic error. Varying the mask size can quantify the error, as well as yielding better estimates of both thickness and horizontal dimensions.

Table 2 presents measured data for different materials of different shapes, sizes and locations with a detector array in accordance with some embodiments described in this document. Focusing on the pure depleted uranium (DU) samples, a variation is shown in scattering/stopping ratio from 1301 to 425, as a function of sample size and location in the detector. Samples of iron (Fe) and steel show raw ratios varying from 550 to 354: significantly less than the average value of those DU samples. This finding suggests that materials can still be discriminated even without compensating for the geometric effects. However, the finite overlap shows that geometric corrections may be used to reduce the occurrence of inaccurate classification. The geometric errors can often be significantly greater than the statistical errors (indicated by the ±quantities in each entry).

TABLE 2

Raw scattering (λ) and stopping data for various objects.

| Run number | Element | Description | Thickness (cm) | λ (mrad* Gev)^2/cm | stopping | Ratio |
|---|---|---|---|---|---|---|
| 201582 | DU | 20 Kg cube | 10.2 | 939 | 0.722 ± 0.097 | 1301 ± 175 |
| 201588 | DU + lead | 20 Kg DU cube in 1" lead shielding | 15.3 | 838 | 0.725 ± 0.056 | 1157 ± 90 |
| 201589 | DU + lead | 20 Kg DU cube in 1" lead shielding | 15.3 | 853 | 0.747 ± 0.058 | 1142 ± 88 |
| 201588 | DU + lead | 7.6 Kg DU in 1" lead shielding | 12.32 | 799 | 0.791 ± 0.081 | 1010 ± 103 |
| 201589 | DU + lead | 7.6 Kg DU in 1" lead shielding | 12.32 | 855 | 0.834 ± 0.111 | 1026 ± 137 |
| 201583 | DU | 20 Kg cube in corner | 10.2 | 1090 | 0.970 ± 0.145 | 1125 ± 168 |
| 201619 | DU | 20 Kg DU cube center | 10 | 1012 | 1.16 ± 0.10 | 876 ± 96 |
| 201620 | DU | 20 Kg DU cube corner | 10 | 541 | 0.953 ± 0.102 | 568 ± 61 |
| 201619 | DU | 7.6 Kg DU cube corner | 7.24 | | | |
| 201620 | DU | 7.6 DU cube center | 7.24 | | | |
| 201607 | DU | 20 Kg DU + 1" lead high in center | 15.06 | 843 | 0.938 ± 0.063 | 899 ± 61 |
| 201608 | DU | 20 Kg DU + 1" lead in corner on floor | 15.06 | 780 | 0.728 ± 0.050 | 1071 ± 74 |
| 201632 | DU + lead | 5 Kg DU + ½" lead | 8.84 | 785 | 1.23 ± 0.13 | 639 ± 69 |
| 20162 | DU | 3.8 Kg | 5.73 | 1363 | 1.42 ± 0.32 | 961 ± 219 |
| 201623 | DU | 5 Kg DU | 6.3 | 664 | 1.56 ± 0.29 | 425 ± 80 |
| 201113 | Pb | 20 Kg 3 pieces | 10.5 | 643 | 0.954 ± 0.132 | 674 ± 93 |
| 201139 | Pb | 8" cube | 20.32 | 805 | 0.64 ± 0.07 | 1258 ± 138 |
| 201208 | Pb | 2" plate | 5.08 | 1107 | 1.77 ± 0.055 | 625 ± 19 |
| 201783 | Pb | 12 × 12 × 11 inch block | 27.94 | 425 | 0.599 ± 0.021 | 710 ± 25 |
| 201113 | W | 2" plates | 5.08 | 1282 | 1.77 ± 0.18 | 724 ± 72 |
| 201321 | W | 3.5" plates | 8.89 | 1157 | 1.34 ± 0.11 | 863 ± 33 |
| 201100 | Fe | Stackomatic | 40.6 | 246 | 0.616 ± 0.011 | 399 ± 7 |
| 201320 | Fe | 12" cube | 30.4 | 266 | 0.595 ± 0.034 | 447 ± 26 |
| 201206 | Fe | 7" stack | 17.8 | 387 | 0.98 ± 0.021 | 395 ± 8 |
| 201219 | Fe | 4" steel shielding with cavity | 20.32 | 410 | 0.89 ± 0.07 | 460 ± 35 |
| 201114 | Fe | 20 Kg cube | 13.6 | 407 | 0.74 ± 0.10 | 550 ± 72 |
| 201139 | Fe | Truck engine composite | c. 48 | 95 | 0.268 ± 0.010 | 354 ± 13 |
| 201114 | Al | 20 Kg cube | 19.4 | 248 | 0.56 ± 0.07 | 443 ± 57 |
| 201701 | nylon | 24 × 24 × 20 inches | 51 | 44.9 | 0.242 ± 0.008 | 178 ± 6 |
| 201511 | Off. paper (0.71 g/cc) | pallet | 132 | 21.2 | 0.079 ± 0.001 | 277 ± 5 |
| 201700 | water | barrel | 80 | 37.7 | 0.126 ± 0.004 | 267 ± 8 |
| 201208 | air | "pallet" | 130 | 10.5 | 0.0620 ± 0.0007 | 169 ± 12 |
| 201672 | ebox | 6107 lb, xy = 112 cm height = 120.3 cm | 120.3 | 42 | 0.170 ± 0.002 | 247 ± 2 |
| 201672 | ebox | Core of ebox | 71 | 158 | 0.477 ± 0.009 | 331 ± 7 |

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

What is claimed are techniques and structures as described and shown, including:

1. A method for characterizing a range of materials based on scattering and stopping of incident cosmic ray charged particles passing through each material, the method comprising:
   for a given material within the range of materials:
      creating a volume of interest (VOI) of the material;
      determining a scattering metric of cosmic ray charged particles interacting with the VOI to represent a first set of cosmic ray charged particles entering and exiting the VOI;
      determining a stopping metric of cosmic ray charged particles interacting with the VOI to represent a second set of cosmic ray charged particles entering and stopping inside the VOI; and
      computing a ratio of the scattering metric to the stopping metric to obtain a scattering-to-stopping ratio for the material; and
   establishing a scattering-stopping relationship of cosmic ray particles for the range of materials based on the determined pairs of the scattering-to-stopping ratio and the associated scattering metric for the range of materials.

2. The method of claim 1, wherein establishing the scattering-stopping relationship includes obtaining a relationship between the scattering-to-stopping ratio and the scattering metric.

3. The method of claim 1, wherein the obtained relationship between the scattering-to-stopping ratio and the scattering metric is substantially linear over the range of materials, and wherein a greater scattering-to-stopping ratio corresponds to a greater density of the associated material.

4. The method of claim 1, wherein determining the scattering metric includes:
   obtaining a set of scattering angles for the first set of cosmic ray charged particles;
   computing an average scattering angle of the set of scattering angles;
   determining an average momentum of the incident cosmic ray charged particles; and
   determining the scattering metric based on the average scattering angle and the average momentum.

5. The method of claim 4, wherein determining the scattering metric includes normalizing the scattering metric by a thickness of the VOI of the material.

6. The method of claim 1, wherein determining the stopping metric includes:
   obtaining a raw stopping number of a set of cosmic ray charged particles entering and stopping inside the VOI;
   obtaining a scattering number of a set of cosmic ray charged particles entering and exiting the VOI; and
   determining the stopping metric by normalizing the raw stopping number by the scattering number to compensate for undetected scattered cosmic ray particles.

7. The method of claim 6, wherein determining the stopping metric includes normalizing the stopping metric by a thickness of the VOI of the material.

8. The method of claim 6, wherein determining the stopping metric includes multiplying the stopping metric by an average momentum of the incident cosmic ray charged particles.

9. The method of claim 1, wherein the cosmic ray charged particles include at least one of cosmic ray muons or cosmic ray electrons.

10. The method of claim 9, wherein the cosmic ray muons are used to characterize metals in the range of materials having densities great than density of aluminum.

11. The method of claim 10, wherein the characterized metals include special nuclear materials (SNM).

12. The method of claim 11, wherein the SNM includes uranium, plutonium or another fissile material used to manufacture nuclear weapons.

13. The method of claim 12, wherein the characterized metals include metals of commercial interests, wherein the metals of commercial interests include one of silver, gold or platinum.

14. The method of claim 9, wherein the cosmic ray electrons are used to characterize materials in the range of materials having densities substantially equal to or less than density of aluminum.

15. A method for identifying the material of a volume of interest (VOI) exposed to cosmic ray particles, the method comprising:
   determining a scattering metric of cosmic ray charged particles interacting with the VOI to represent a first set of cosmic ray particles entering and exiting the VOI;
   determining a stopping metric of cosmic ray charged particles interacting with the VOI to represent a second set of cosmic ray charged particles entering and stopping inside the VOI;
   computing a ratio of the scattering metric to the stopping metric to obtain a scattering-to-stopping ratio for the VOI; and
   comparing the determined pair of scattering-to-stopping ratio and the scattering metric against an established relationship between the scattering-to-stopping-ratio and the scattering metric for a range of known materials to determine whether the material of the VOI matches a material in the range of known materials.

16. The method of claim 15, wherein determining the scattering metric includes:
   obtaining a set of scattering angles for the first set of cosmic ray charged particles;
   computing an average scattering angle of the set of scattering angles;
   determining an average momentum of the incident cosmic ray charged particles; and
   determining the scattering metric based on the average scattering angle and the average momentum.

17. The method of claim 16, wherein determining the scattering metric includes normalizing the scattering metric by a thickness of the VOI.

18. The method of claim 15, wherein determining the stopping metric includes:
   obtaining a raw stopping number of a set of cosmic ray charged particles entering and stopping inside the VOI;
   obtaining a scattering number of a set of cosmic ray charged particles entering and exiting the VOI; and
   determining the stopping metric by normalizing the raw stopping number by the scattering number to compensate for the undetected scattered cosmic ray charged particles.

19. The method of claim 18, wherein determining the stopping metric includes normalizing the stopping metric by a thickness of the VOI.

20. The method of claim 18, wherein determining the stopping metric includes multiplying the stopping metric by an average momentum of the incident cosmic ray charged particles.

21. The method of claim 15, wherein the cosmic ray charged particles include cosmic ray muons and cosmic ray electrons.

22. The method of claim 21, wherein the cosmic ray muons are used to detect the VOI for target metals having densities great than density of aluminum.

23. The method of claim 22, wherein the target metals include special nuclear materials (SNM).

24. The method of claim 23, wherein the SNM includes uranium, plutonium or another fissile material used to manufacture nuclear weapons.

25. The method of claim 22 wherein the target metals include metals of commercial interests, wherein the metals of commercial interest includes one of silver, gold or platinum.

26. The method of claim 21, wherein the cosmic ray electrons are used to detect the VOI for target metals having densities substantially equal to or less than the density of aluminum.

27. The method of claim 21, wherein after identifying the material of the VOI, the method further comprises inferring a thickness of the VOI based on an established relationship between the scattering-to-stopping-ratio and a normalized stopping metric per unit thickness for the range of known materials.

28. A cosmic ray based detection system comprising:
   a position sensitive incoming cosmic ray charged particle detector configured to detect incident cosmic ray charged particles entering a volume of interest;
   a position sensitive outgoing cosmic ray charged particle detector configured to detect outgoing cosmic ray charged particles exiting the volume of interest; and
   a processing unit communicatively coupled to the position sensitive incoming cosmic ray charged particle detector and the position sensitive outgoing cosmic ray charged particle detector, the processing unit configured to perform the following:
      receiving signals from the position sensitive incoming cosmic ray charged particle detector and the position sensitive outgoing cosmic ray charged particle detector, the received signals indicative of scattering and stopping of the incoming and outgoing cosmic ray charged particles,
      determining a scattering metric and a stopping metric based on respective signals indicative of scattering and stopping of the incoming and outgoing cosmic ray charged particles,
      determining a relationship between the scattering metric and a ratio of the scattering metric to the stopping metric, and
      identifying a material associated with the volume of interest based on the determined relationship.

29. The cosmic ray based detection system of claim 28, wherein the processing unit is configured to determine a thickness of the identified material based on the determined relationship.

* * * * *